US012496221B2

(12) United States Patent
McClunan et al.

(10) Patent No.: US 12,496,221 B2
(45) Date of Patent: Dec. 16, 2025

(54) SHUNT AND METHOD FOR TREATING GLAUCOMA

(71) Applicant: LIQID MEDICAL PROPRIETARY LIMITED, Cape Town (ZA)

(72) Inventors: Daemon Bruce McClunan, Cape Town (ZA); Joshua David Fischer, Cloetesville (ZA)

(73) Assignee: LIQID MEDICAL PROPRIETARY LIMITED, Cape Town (ZA)

(*) Notice: Subject to any disclaimer, the term of this patent is extended or adjusted under 35 U.S.C. 154(b) by 457 days.

(21) Appl. No.: 18/008,630

(22) PCT Filed: Jun. 10, 2021

(86) PCT No.: PCT/IB2021/055110

§ 371 (c)(1),
(2) Date: Dec. 6, 2022

(87) PCT Pub. No.: WO2021/250609

PCT Pub. Date: Dec. 16, 2021

(65) Prior Publication Data

US 2023/0218440 A1 Jul. 13, 2023

(30) Foreign Application Priority Data

Jun. 11, 2020 (ZA) ................................ 2020/03488

(51) Int. Cl.
*A61F 9/007* (2006.01)

(52) U.S. Cl.
CPC ................................ *A61F 9/00781* (2013.01)

(58) Field of Classification Search
CPC ................................................... A61F 9/00781
See application file for complete search history.

(56) References Cited

U.S. PATENT DOCUMENTS

| | | | |
|---|---|---|---|
| 2004/0254517 | A1 | 12/2004 | Quiroz-Mercado et al. |
| 2006/0079828 | A1 | 4/2006 | Brown |
| 2014/0236066 | A1 | 8/2014 | Horvath et al. |
| 2015/0265469 | A1 | 9/2015 | Olson et al. |
| 2019/0000673 | A1 | 1/2019 | Fjield et al. |

OTHER PUBLICATIONS

Gedde SJ. Management of glaucoma after retinal detachment surgery. Curr Opin Ophthalmol 2002; 13(2) 103-9. (Year: 2002).*

* cited by examiner

*Primary Examiner* — Leslie R Deak
(74) *Attorney, Agent, or Firm* — Harness, Dickey & Pierce, P.L.C.

(57) ABSTRACT

A shunt 200 for treating glaucoma in a patient during and/or after vitreoretinal surgery involving the use of a tamponading agent comprising a gas or oil bubble 50. The shunt includes a tubular body 12 having a proximal end 14 which is implantable in the vitreous cavity C of a patient and a distal end which is implantable in the subarachnoid space of the patient. The tubular body defines a lumen 18 extending between the distal and proximal ends. The shunt includes an occlusion body 32 defining a number of micro-passages 34 inflow communication with the lumen 18. The micro-passages are configured in terms of their size and number to provide sufficient surface tension and viscosity resistance in order to prevent the tamponading agent from passing through the micro-passages into the lumen, yet allow sufficient aqueous fluid from the vitreous cavity to travel along the micro-passages into the lumen 18 in order to regulate intraocular pressure.

3 Claims, 12 Drawing Sheets

SHUNT AND METHOD FOR TREATING GLAUCOMA

CROSS-REFERENCE TO RELATED APPLICATIONS

This application is a U.S. national stage filing under 35 U.S.C. § 371 of International Application No. PCT/IB2021/055110, filed on Jun. 10, 2021, which claims the benefit of, and priority to, South African Patent Application No. 2020/03488, filed on Jun. 11, 2020. The entire disclosure of each of the above applications is incorporated herein by reference.

FIELD OF INVENTION

This invention relates to a shunt for treating glaucoma in a patient. The invention relates particularly to a shunt for draining excess aqueous fluid from an ocular chamber into an extra-ocular space such as the orbital subarachnoid space in a patient undergoing vitreoretinal surgery involving the use of a tamponading agent. The invention relates also to a method for treating glaucoma in a patient undergoing vitreoretinal surgery involving the use of a tamponading agent, including the use of a shunt for draining excess aqueous fluid from an ocular chamber into an extra-ocular space such as the orbital subarachnoid space in the patient.

Any reference in this specification to an "ocular chamber" must be interpreted as a reference to the anterior chamber, posterior chamber and vitreous cavity of the ocular globe, only.

Any reference in this specification to an "extra-ocular space" must be interpreted as a reference to an ocular space located externally of the ocular chamber, such as a subarachnoid space, Schlemm's canal, suprachoroidal space and a subconjunctival space.

BACKGROUND TO INVENTION

A shunt device suitable for use following vitreoretinal surgery where a tamponading agent has been used needs to overcome the following difficulties:

- Prevent tamponading agents from passing through the shunt devices from an intraocular cavity to an extra-ocular cavity; and
- Regulate the flow rate of aqueous fluid from the ocular chambers into the subarachnoid space so as to prevent over or under drainage of aqueous fluid.

The implantation of a shunt connecting the ocular chambers and the subarachnoid space surrounding the optic nerve by penetrating through the posterior wall of the ocular globe in a patient suffering from glaucoma, for drainage of excess aqueous fluid, is a procedure which, in order to be successful, needs to overcome the following difficulties:

- limit damage to important retinal nerve fibres;
- prevent damage to the optic nerve head blood supply; and
- reliably insert into the subarachnoid space.

The ocular globe of the eye has a tough outer layer comprised of the sclera and the cornea. The ocular globe maintains an internal pressure known as the intraocular pressure which normally varies between 10 mmHg and 21 mmHg. The intraocular pressure needs to be controlled within a defined range in order for the eye to function normally.

Intraocular pressure is regulated by maintaining a balance between volumes of aqueous fluid produced and drained from the anterior chamber of the ocular globe. Aqueous fluid is produced by the ciliary body and drained through the trabecular and uveoscleral pathways. If an imbalance occurs in the amount of aqueous produced or drained from the ocular globe, then the intraocular pressure becomes too high.

The lamina cribrosa separates the intraocular and subarachnoid fluid compartments. The presence of raised intraocular pressure or low intracranial pressure results in a large pressure differential across the lamina cribrosa (translaminar pressure). This causes damage to the optic nerve head due to biomechanical, blood flow and axoplasmic flow factors resulting in the condition known as glaucoma. Glaucoma causes irreversible visual field defects. These defects enlarge until a patient's field of view is severely restricted. In the end stage of the disease, total vision loss occurs. Glaucoma is a leading cause of blindness worldwide. If the intraocular pressure remains very high, the eye can become persistently painful and may need to be removed.

The orbital subarachnoid space surrounding the optic nerve is formed between the optic nerve and the sheath and is filled with cerebrospinal fluid. Cerebrospinal fluid has a chemical composition comparable to that of the aqueous fluid of the eye. The pressure within cerebrospinal fluid normally varies between 5 mmHg and 15 mmHg.

Macular retinal nerve fibres which are essential for fine vision enter the optic nerve head from the lateral side. The optic nerve head receives its blood supply predominantly from the Paraoptic Short Posterior ciliary arteries (PSPCA). The PSPCA's enter the sclera in the medial, lateral or occasionally, superior quadrants. Branches of the PSPCA's pierce the sclera. After piercing the sclera, the PSPCA's branch to create the elliptical Circle of Zinn-Haller (CZH) which is located in the region of the paraoptic sclera. The CZH is elliptical in shape. CZH blood vessels may be located up to 1 mm from the optic nerve head in the medial and lateral quadrants, but are usually closer, within 0.5 mm from the optic nerve head, in the inferior and superior quadrants.

Glaucoma may also be induced or worsened in the case of patients having underlying glaucoma, by vitreoretinal surgery. Vitreoretinal surgery is a surgical procedure where the posterior vitreous cavity of the eye is entered through incisions made through in the pars plana region of the eye. Access ports are left in place during surgery. Patients undergoing vitreoretinal surgery often have underlying glaucoma or may suffer glaucoma induced by vitreoretinal surgery. A common indication for vitreoretinal surgery is retinal detachment. To repair a retinal detachment, the vitreous gel is first removed using a vitrectomy device. The retinal detachment is then repaired using a number of mechanisms. Frequently, the vitreous chamber is filled with a bubble of gas or high-density silicone oil to act as a tamponading agent holding the previously detached retina against the ocular globe so that adhesion may occur. These tamponades are left in the vitreous cavity, where they remain for a period of time following surgery. Tamponade gasses typically dissolve spontaneously over one to 8 weeks. Silicone oil is manually removed after a period of weeks to months. During vitreoretinal surgery, ocular pressures may be artificially increased up to 60 mmHg. In the days or weeks following surgery, ocular pressures are often between 20 and 40 mmHg. Existing glaucoma devices are either unsuitable for implantation during vitreoretinal surgery or are not suitable for use in the presence of tamponading agents. This means that patients may suffer optic nerve damage from high post-operative ocular pressures and may need to undergo multiple surgeries to control glaucoma induced by vitreoretinal surgery.

It is an object of the present invention to provide a shunt which allows for drainage of excess aqueous fluid from the ocular chambers into the orbital subarachnoid space, while overcoming the difficulties referred to hereinabove. It is also an object of the present invention to provide a method for treating glaucoma in a patient including the use of a shunt for draining excess aqueous fluid from the ocular chambers into the subarachnoid space of the patient, which addresses the difficulties referred to hereinabove.

SUMMARY OF INVENTION

According to a first aspect of the invention there is provided a shunt for treating glaucoma in a patient during and/or after vitreoretinal surgery involving the use of a tamponading agent, the shunt including a tubular body having a proximal end which is implantable in an ocular chamber of a patient and a distal end which is implantable in an extra-ocular space of the patient, the tubular body defining a lumen extending between the distal and proximal ends, the shunt including occlusion means for at least partially occluding the lumen so as to prevent the tamponading agent from entering the extra-ocular space.

In use, the proximal end of the shunt may be implantable in the vitreous cavity of the eye of a patient.

The shunt may have at least one external stop formation for resisting migration of the tubular body following insertion of the tubular body into the subarachnoid space. In one embodiment, the stop formation may be in the form of a protuberance which projects outwardly from the tubular body while in another embodiment, the stop formation may be in the form of an inwardly-extending recess.

A distal end region of the tubular body may be tapered towards the distal end of the tubular body. More specifically, the distal end region of the tubular body may have a rounded, non-cutting surface profile so as to limit damage to retinal nerve fibres when implanting the shunt.

The tubular body may define a proximal opening at the proximal end thereof, leading into the lumen. The tubular body may define a distal opening at the distal end thereof, leading into the lumen. Alternatively, or in addition, the tubular body may define one or more distal openings in a side wall of the distal end region of the tubular body, leading into the lumen.

The shunt may incorporate an elutable therapeutic substance. More specifically, the elutable therapeutic substance may be an antibiotic substance for preventing the spread of an infection between the ocular chamber and the extra-ocular space or an anticlotting agent for preventing blockage of blood vessels or the lumen of the tubular body by blood clots.

In a first embodiment of the invention, wherein the shunt is adapted for use in vitreoretinal surgery involving the use of a tamponading agent comprising a gas or oil bubble, the occlusion means comprises a valve member which is located adjacent the proximal end of the tubular body and which is acted upon by surface tension of the gas or oil bubble causing displacement of the valve member into a condition where the valve member at least partially occludes the lumen.

In a first example of the first embodiment, the valve member may comprise a flap valve which is hingedly connected to the tubular body at its proximal end, the flap valve being hingedly displaceable between a closed position wherein the flap at least partially occludes the lumen when acted upon by the gas or oil bubble, preventing the gas or oil bubble from passing into the lumen and an open position wherein the lumen is not occluded, allowing aqueous fluid to flow along the lumen in order to adequately regulate intraocular pressure. The flap valve may be connected to the tubular body in an arrangement wherein the flap valve is biased into the open position.

In a second example of the first embodiment, the valve member may comprise a flexible tube valve which is sealingly connected to the tubular body at its proximal end, the tube valve defining an internal passage which is in flow communication with the lumen of the tubular body. The tube valve may be configured to bend when acted upon by the surface tension of a gas bubble or oil bubble thereby at least partially occluding the passage and preventing the gas or oil bubble from passing along the passage and entering the lumen of the tubular body. The tube valve may be resiliently deformable so as to be displaceable between a closed position wherein the tube valve is bent so as to at least partially occlude the passage thereof when acted upon by the gas or oil bubble, preventing the gas or oil bubble from passing into the passage and an open position wherein the passage is not occluded, allowing aqueous fluid to flow along the passage into the lumen of the tubular body in order to adequately regulate intraocular pressure.

The tube valve may comprise a resiliently deformable first tube valve element which is sealingly connected to the tubular body and a deformable second tube valve element which is connected to an end of the first tube valve element, the first and second tube valve elements define a common passage which is in flow communication with the lumen of the tubular body. The second valve element may be of a relatively stiffer construction than the construction of the first tube valve element, thereby providing the tube valve with a structure having variable stiffness wherein a distal end region of the tube valve defined by the second valve element is stiffer than a proximal end region of the tube valve defined by the first valve element. More specifically, the second tube valve element may be displaceable between a valve closing position wherein the second tube valve element bends when acted upon by a gas or oil bubble, causing a bending force to be exerted in turn on the first tube valve element resulting in bending of the first tube valve element and causing the passage defined by the first tube valve element to at least partially occlude, thereby preventing the gas or oil bubble from passing into the passage and the lumen of the tubular body; and a valve opening position wherein the second tube valve element is not acted upon by the gas or oil bubble, allowing the first tube valve element to return to a naturally open position wherein the passage defined thereby is not occluded, allowing aqueous fluid to flow along the lumen of the tubular body in order to adequately regulate intraocular pressure.

In a second embodiment of a shunt in accordance with the invention, wherein the shunt is adapted for use in vitreoretinal surgery involving the use of a tamponading agent comprising a gas or oil bubble, the occlusion means may include a foraminous body covering the lumen of the tubular body adjacent the proximal end thereof. More particularly, the foraminous body may define a number of micro-passages leading into the lumen, wherein the micro-passages are configured to provide sufficient surface tension and viscosity resistance in order to prevent tamponading agents comprising gas bubbles or oil bubbles from passing through the micro-passages into the lumen, yet allow sufficient aqueous fluid to travel along the micro passages to the lumen in order to regulate intraocular pressure. More specifically, the number and size of the micro-passages provide sufficient surface tension and viscosity resistance in order to prevent the tamponading agents from passing through the micro-passages into the lumen. The micro-passages may be configured for use in regulating intraocular pressures in the range between 5 mmHg and 60 mmHg. The foraminous body may be of a hydrophilic material for use with an oil or gas bubble tamponading agent for promoting a flow of aqueous fluid into the lumen. For use with an oil bubble tamponading agent, the occlusion body may additionally or alternatively, be of an oleophobic material for resisting a flow of oil into the lumen.

In a third embodiment of a shunt in accordance with the invention, wherein the shunt is adapted for use in vitreoretinal surgery involving the use of a tamponading agent, the occlusion means may comprise a plug which is removably attached to the proximal end of the tubular body in order to occlude the lumen, preventing the tamponading agent from passing into the lumen. More specifically, the plug is fitted to the tubular body during a vitreoretinal surgical procedure by a surgeon and thereafter removed once the tamponading agent is no longer present in the vitreous cavity.

In a fourth embodiment of a shunt in accordance with the invention, wherein the shunt is adapted for use in vitreoretinal surgery involving the use of a tamponading agent, the occlusion means may comprise a dissolvable membrane which is attached to the tubular body at its proximal end so as to cover the proximal end, thereby occluding the lumen and preventing the tamponading agent from passing into the lumen. More specifically, the membrane is of a material which dissolves over a period of time so as to no longer occlude the lumen of the tubular body, coinciding with the tamponading agent no longer being present.

In a fifth embodiment of a shunt in accordance with the invention, wherein the shunt is adapted for use in vitreoretinal surgery involving the use of a tamponading agent, the occlusion means may comprise a laserable membrane which is attached to the proximal end of the tubular body in order to occlude the lumen, preventing the tamponading agent from passing into the lumen. More specifically, the membrane is punctured by a surgeon using a laser once the tamponading agent is no longer present in the vitreous cavity.

According to a second aspect of the invention there is provided a method for treating glaucoma in a patient during and/or after vitreoretinal surgery, the method including:

- providing a shunt as described and defined hereinabove in accordance with the first aspect of the invention;
- making at least one incision in the pars plana region of the sclera;
- removing the vitreous jelly from the vitreous cavity via the incision and replacing it with a saline solution;
- advancing the distal end of the shunt through retinal nerve fibres and scleral tissue to enter the orbital subarachnoid space between the optic nerve and optic nerve sheath;
- leaving the proximal end of the shunt within the vitreous cavity; and
- replacing an amount of saline solution in the vitreous cavity with a surgical tamponading agent in the form of gas or oil.

The distal end of the shunt may be advanced through scleral tissue in the inferior or superior quadrants approximately 0.5-1.5 mm from the optic nerve head in order to avoid important blood vessels The distal end of the shunt may be advanced through retinal nerve fibres in the inferior, medial or superior quadrants to limit damage to important macular retinal nerve fibres.

BRIEF DESCRIPTION OF THE DRAWINGS

Further features of the invention are described hereinafter by way of a non-limiting example of the invention with reference to and as illustrated in the accompanying diagrammatic drawings. In the drawings.

DETAILED DESCRIPTION OF THE INVENTION

Figure 1:
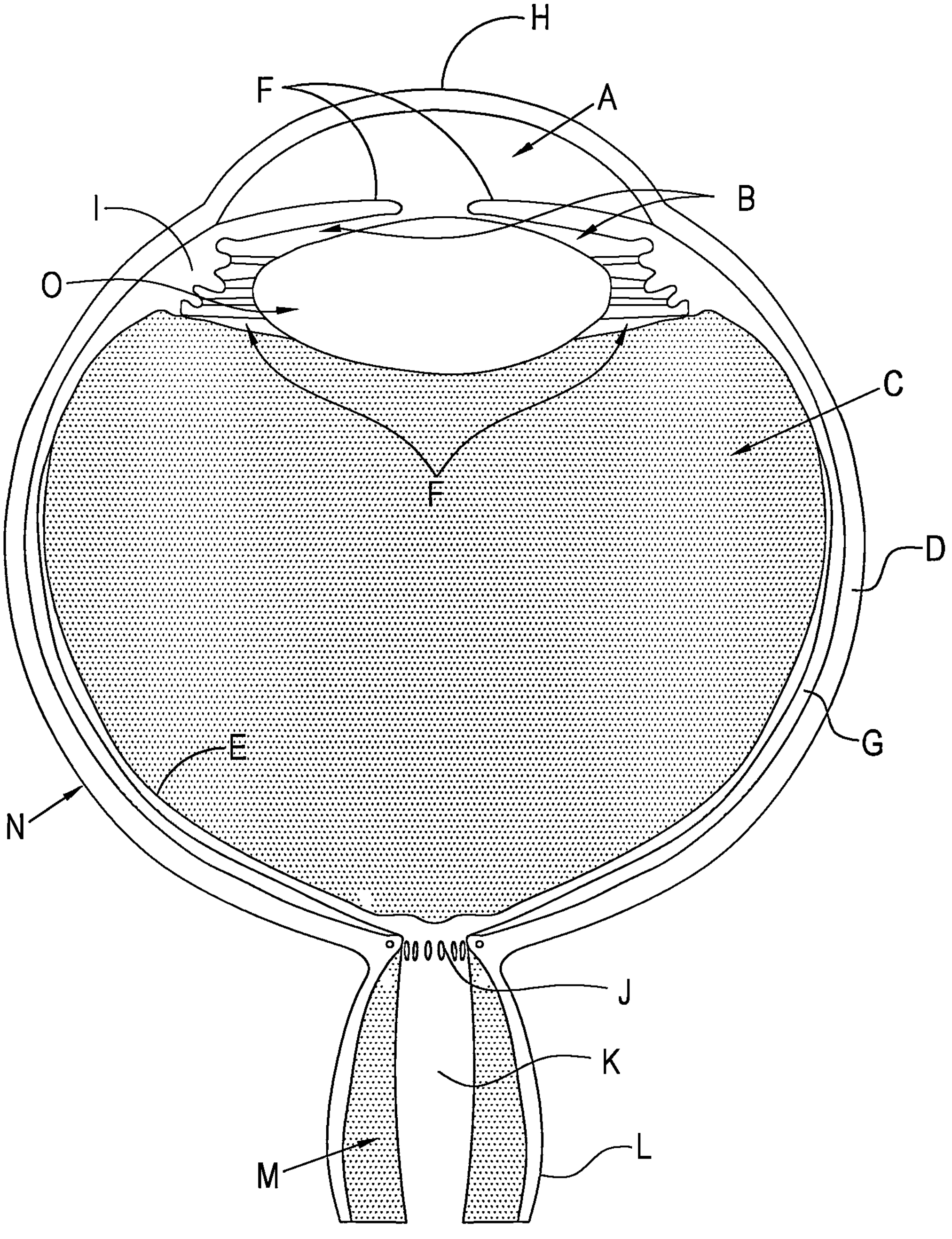
FIG. 1 shows a cross-sectional view of a human eye.

With reference to FIG. 1 of the drawings, a cross-sectional view illustrating anatomical parts of a human eye 2 which are required for use in the description which follows below, comprises:

A: Anterior chamber filled with aqueous fluid
B: Posterior chamber filled with aqueous fluid
C: Vitreous cavity filled with vitreous jelly
D: Sclera
E: Retina
F: Zonule fibres
G: Choroid
H: Cornea
I: Ciliary body
J: Lamina cribrosa
K: Optic nerve L: Optic nerve sheath M: Orbital subarachnoid space filled with cerebrospinal fluid N: Ocular globe O: Lens With reference to FIGS. 2 to 8A of the drawings, a first example of a first embodiment of a shunt in accordance with the invention, is designated generally by the reference numeral 10. The shunt 10 is adapted for implantation in the human body so as to provide for flow communication between aqueous fluid in the vitreous cavity C of the eye and cerebrospinal fluid in the orbital subarachnoid space M surrounding the optic nerve K. More specifically, the shunt is configured for treating glaucoma in a patient during and/or after vitreoretinal surgery involving the use of a tamponading agent. The shunt 10 when implanted, regulates intraocular pressure in the eye of the patient. For the treatment of glaucoma, the shunt permits aqueous fluid to drain from the vitreous cavity C of the eye into the subarachnoid space M, thereby reducing intraocular pressure.

The shunt 10 includes a tubular body 12 having a proximal end 14 which is implantable in the vitreous cavity C of a patient and a distal end 16 which is implantable in an extra-ocular space of the patient such as the subarachnoid space M of the patient. The tubular body defines a lumen 18 extending between the distal and proximal ends.

The shunt defines three stop formations in the form of longitudinally-spaced circumferential grooves 20 for resisting migration of the tubular body following insertion of the tubular body into the subarachnoid space.

A distal end region of the tubular body tapered towards the distal end 16 of the tubular body. The distal end of the tubular body has a pencil point, non-cutting surface profile.

The tubular body defines a proximal opening 22 at the proximal end 14, leading into the lumen. The tubular body defines four distal openings 24 in a side wall of the distal end region, leading into the lumen.

The tubular body is of a biocompatible material polymer and may incorporate an elutable therapeutic substance such as an antibiotic substance for preventing the spread of an infection between the ocular chamber and the subarachnoid space or an anticlotting agent for preventing blockage of adjacent blood vessels or the lumen of the tubular body by blood clots.

Figure 2:
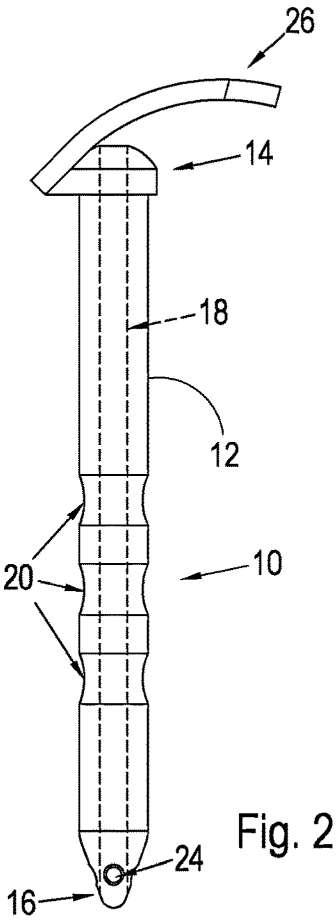
FIG. 2 shows a side view of a shunt in accordance with a first example of a first embodiment of the invention with the flap valve in an open position.
Figure 3:
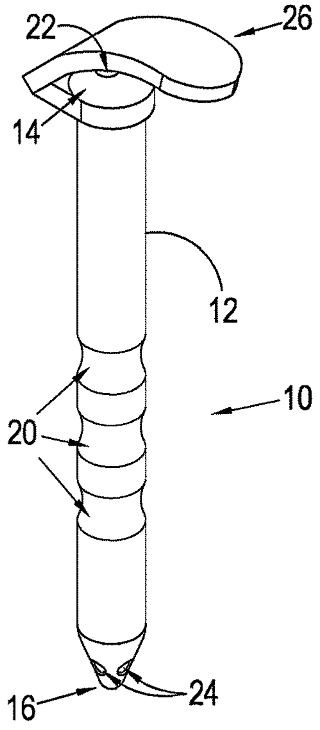
FIG. 3 shows a three-dimensional view of the shunt of FIG. 2.
Figure 4:
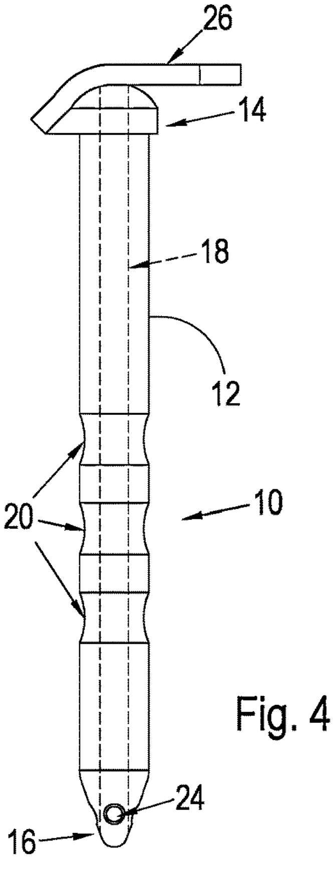
FIG. 4 shows a side view of the shunt of FIG. 2 with the flap valve in a closed position.
Figure 5:
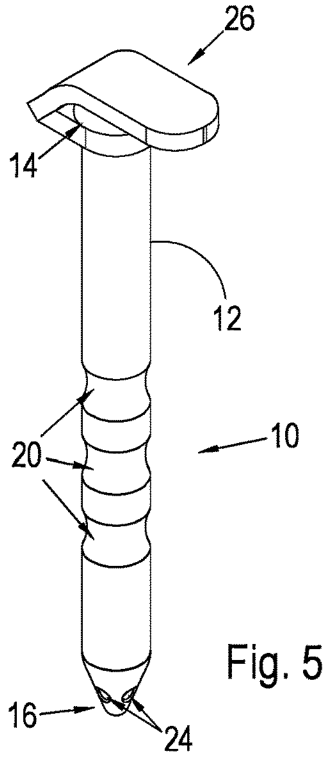
FIG. 5 shows a three-dimensional view of the shunt of FIG. 4.
Figure 6:
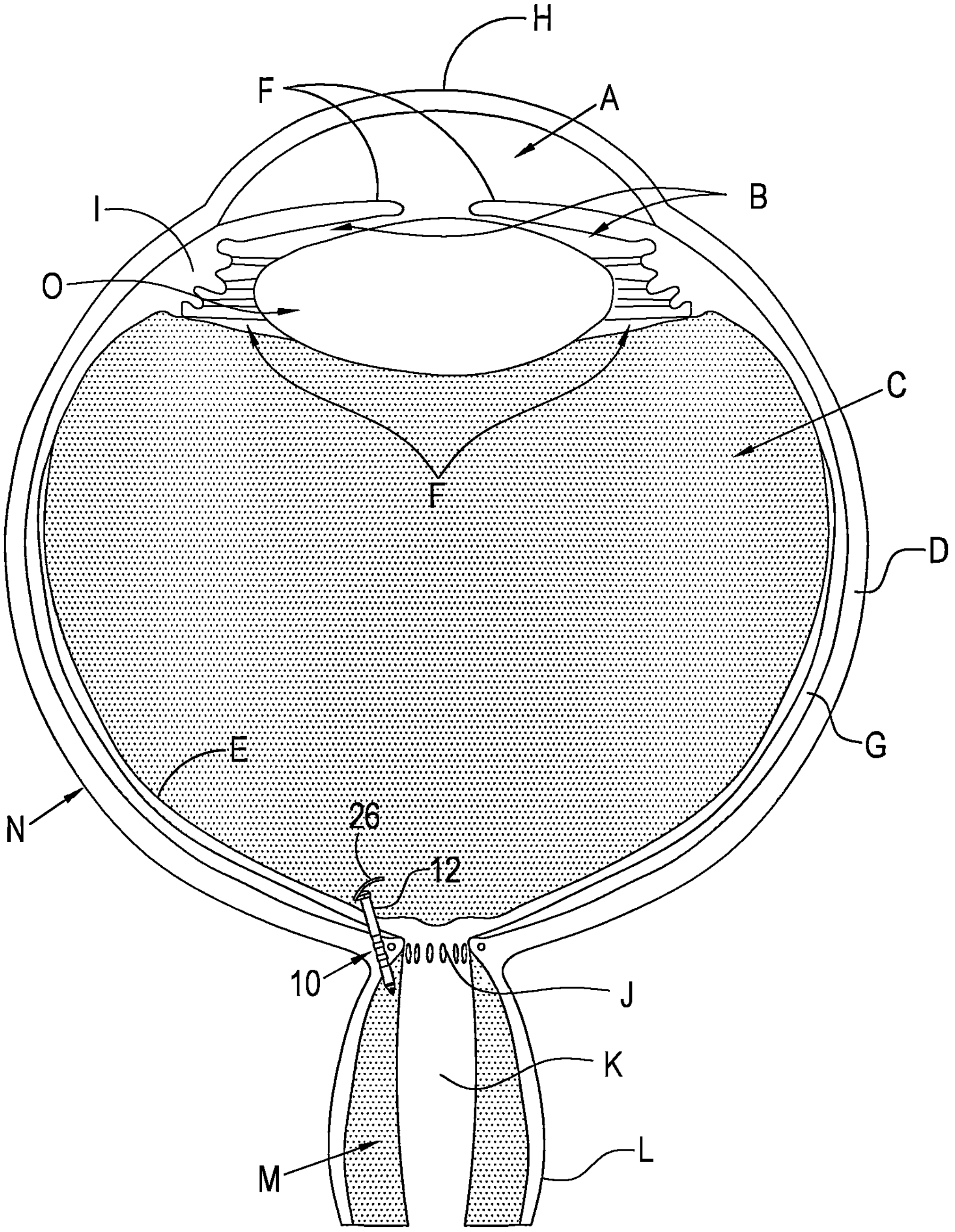
FIG. 6-8A illustrate the manner in which the shunt of FIG. 2 is implanted and used during a vitreoretinal surgical procedure including the use of a gas bubble as a tamponading agent.
Figure 7:
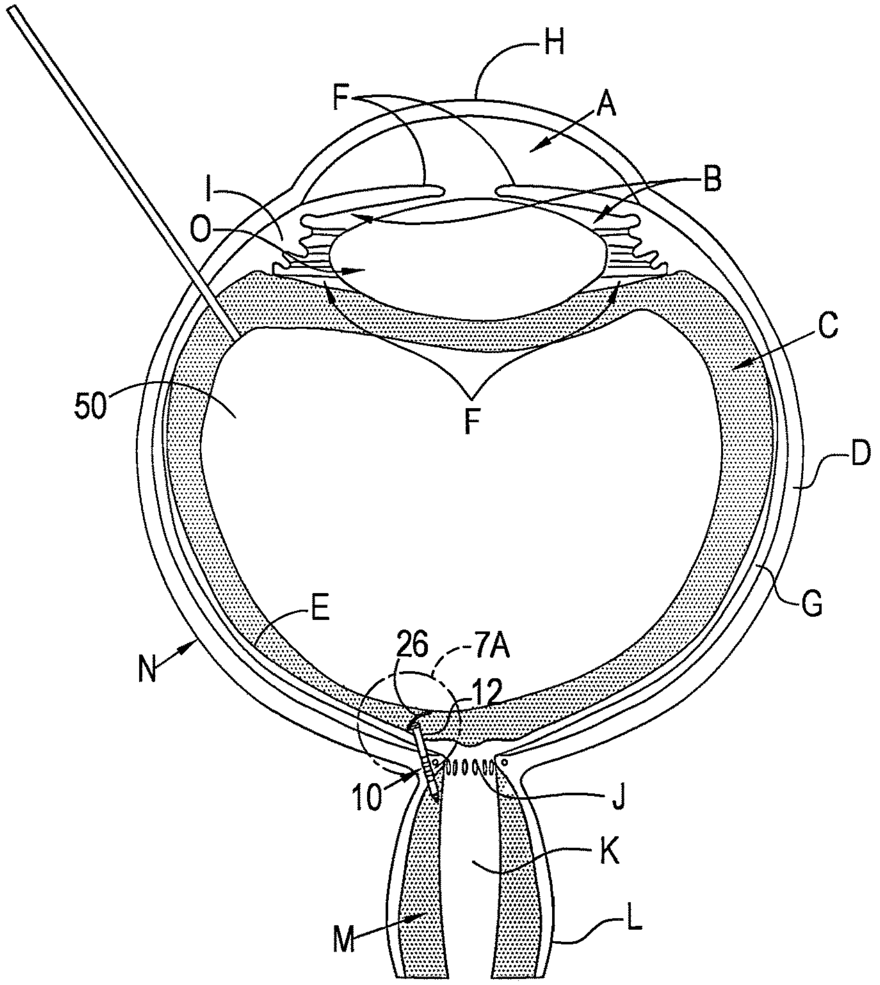
Figure 7A:
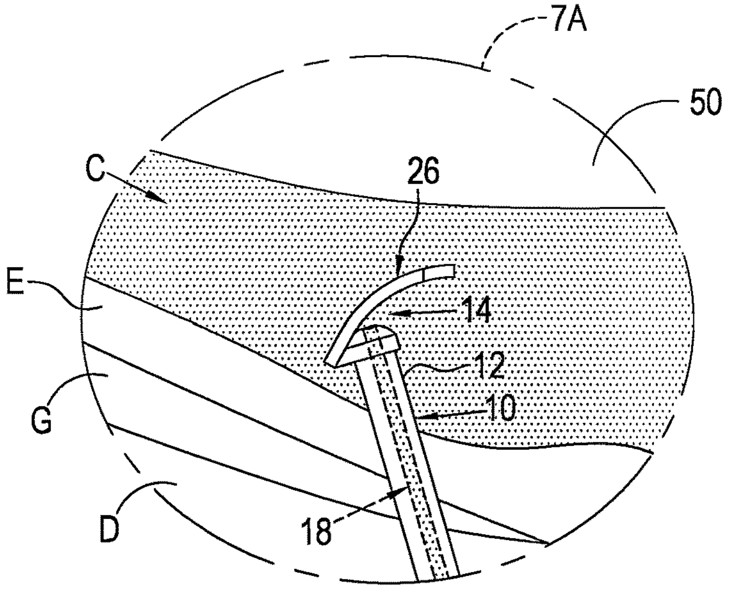
Figure 8:
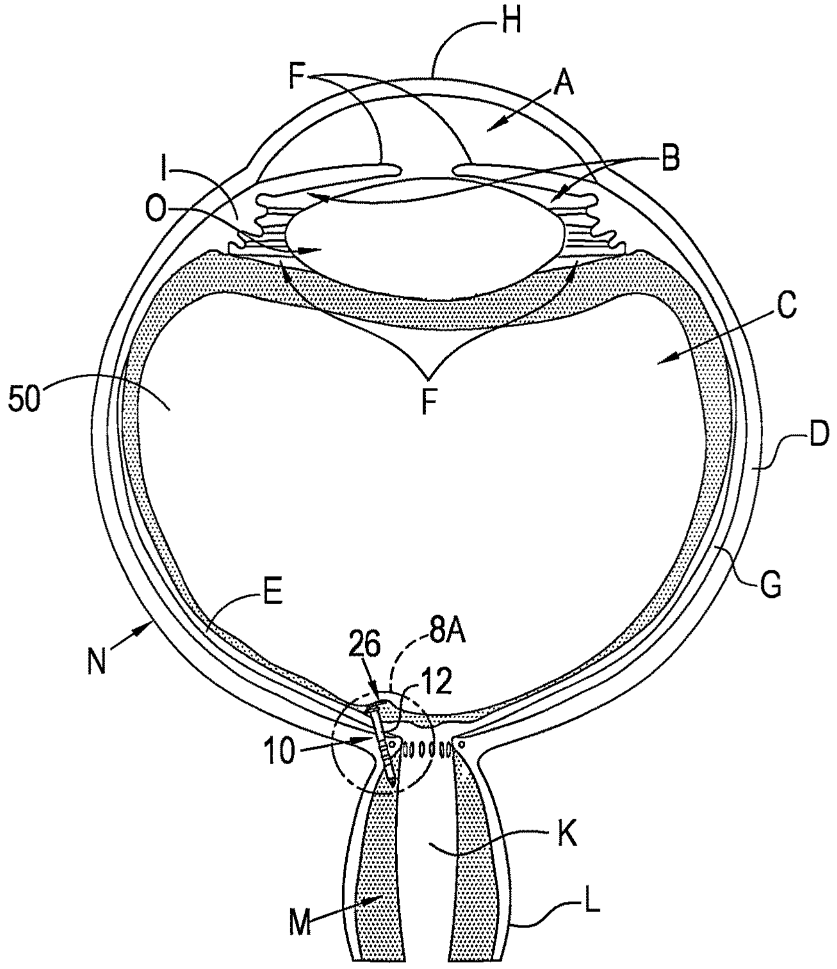
Figure 8A:
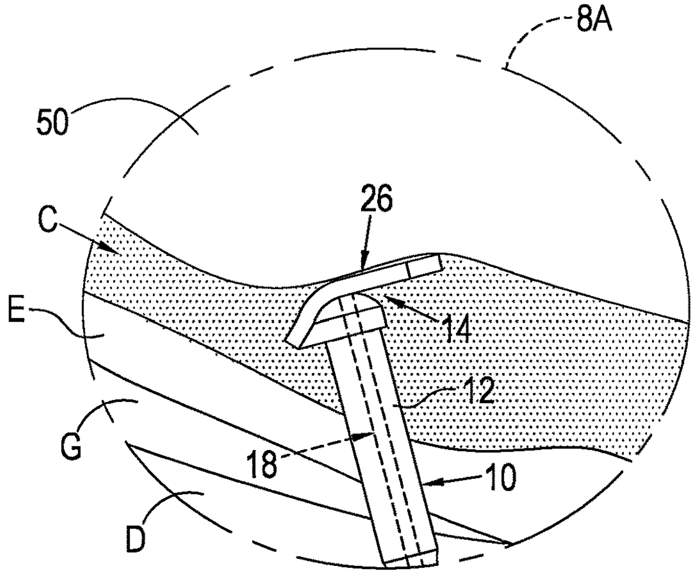
Figure 9:
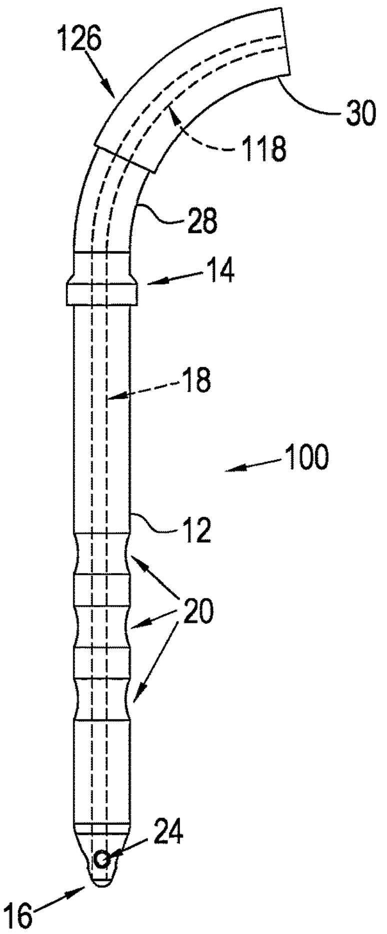
FIG. 9 shows a side view of a second example of the first embodiment of a shunt in accordance with the invention, in an undeformed state wherein the lumen is open.
Figure 10:
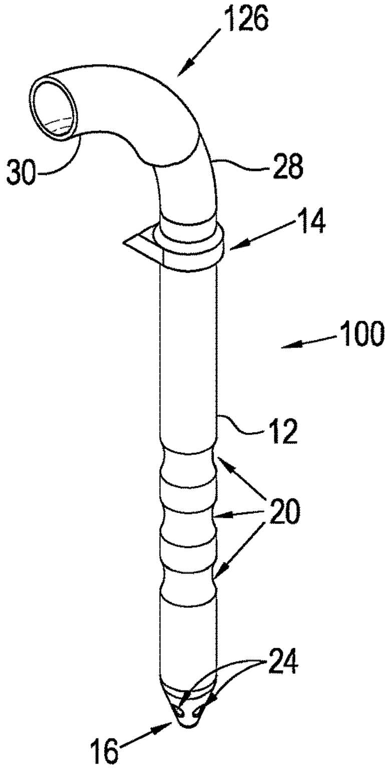
FIG. 10 shows a three-dimensional view of the shunt of FIG. 9.
Figure 11:
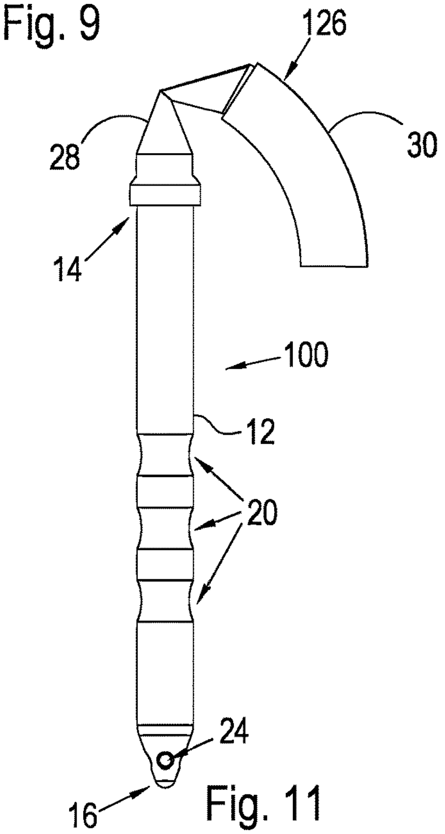
FIG. 11 shows a side view of the shunt of FIG. 9 in a bent deformed state wherein the lumen is occluded.
Figure 12:
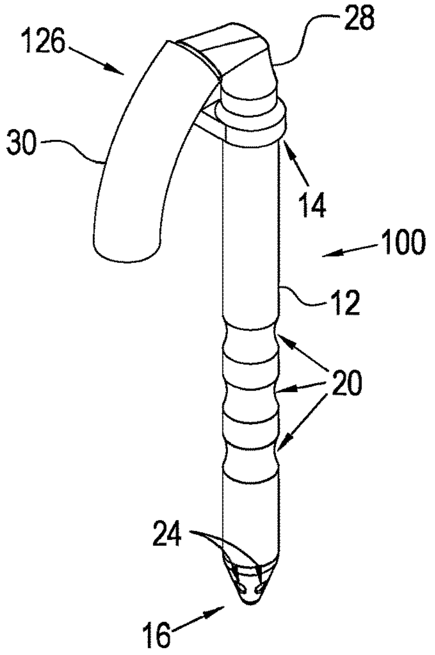
FIG. 12 shows a three-dimensional view of the shunt of FIG. 11.
Figure 13:
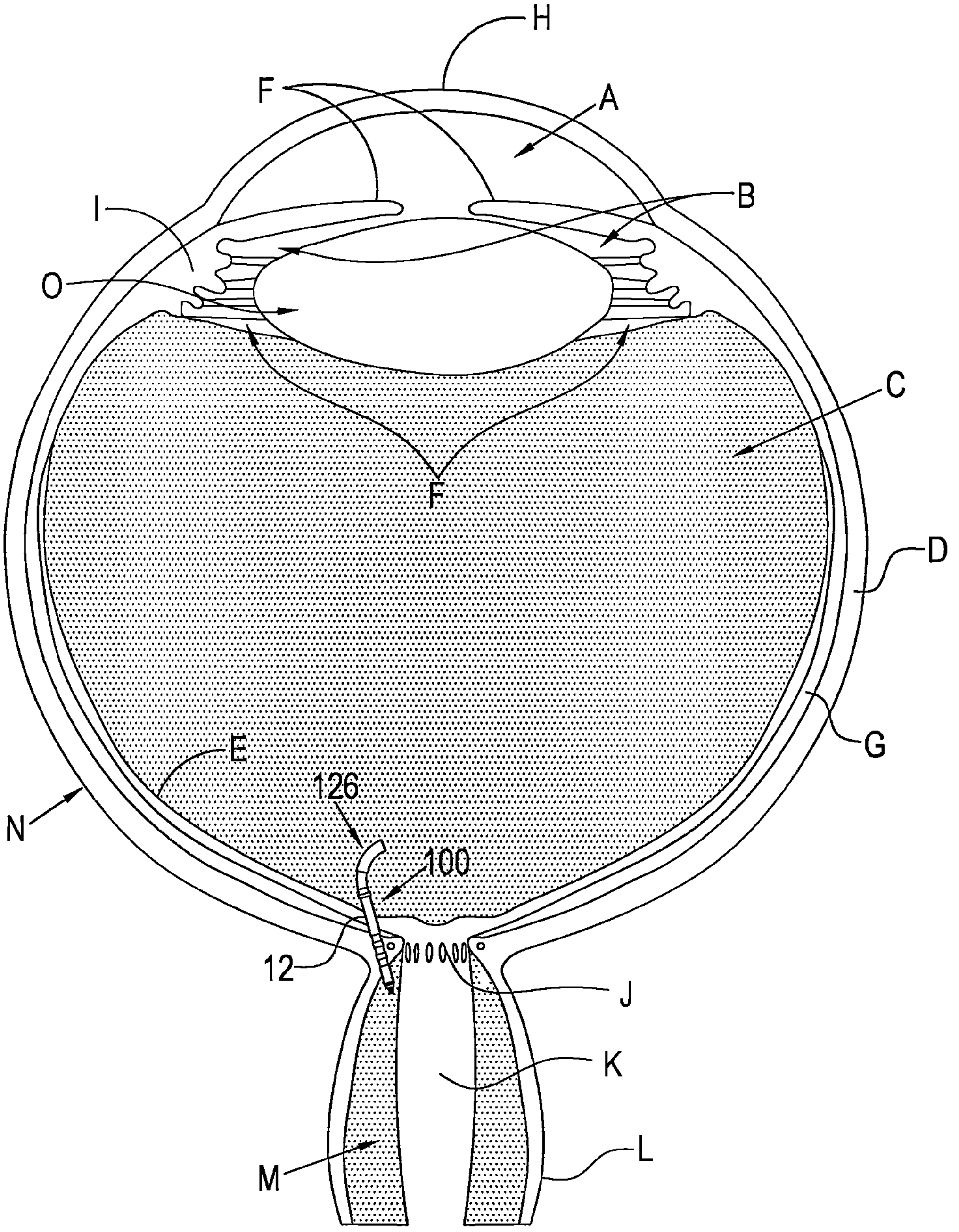
FIGS. 13-15A illustrate the manner in which the shunt of FIG. 9 is implanted and used during a vitreoretinal surgical procedure including the use of a gas bubble as a tamponading agent.
Figure 14:
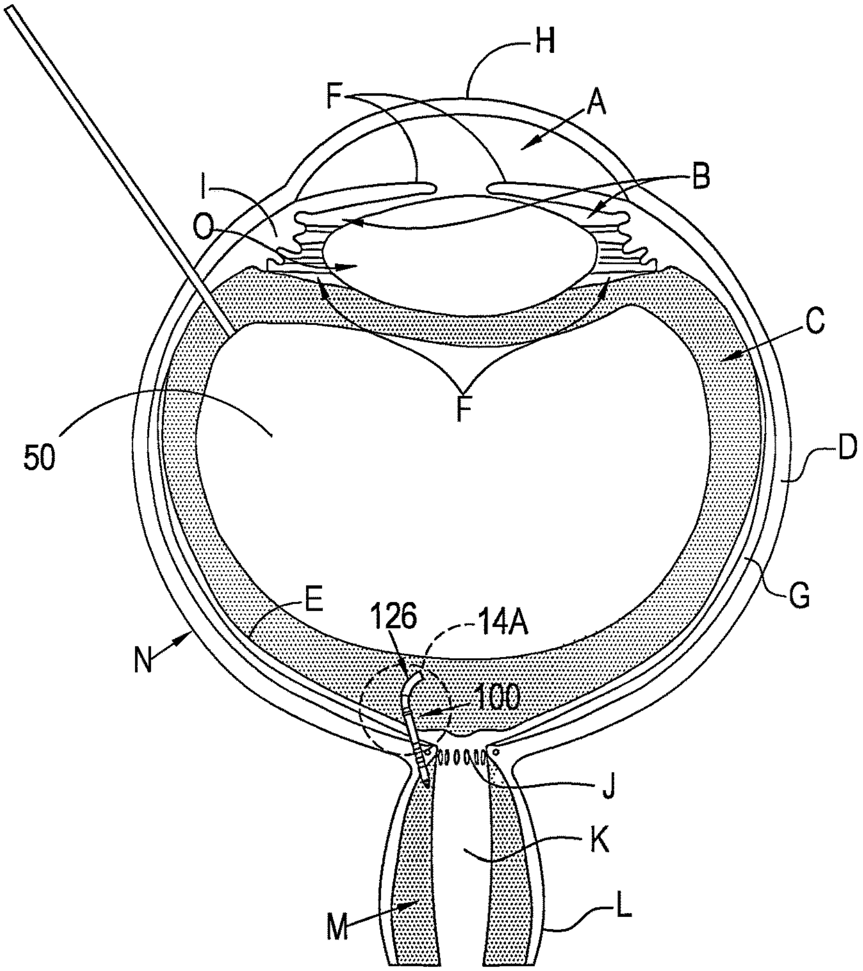
Figure 14A:
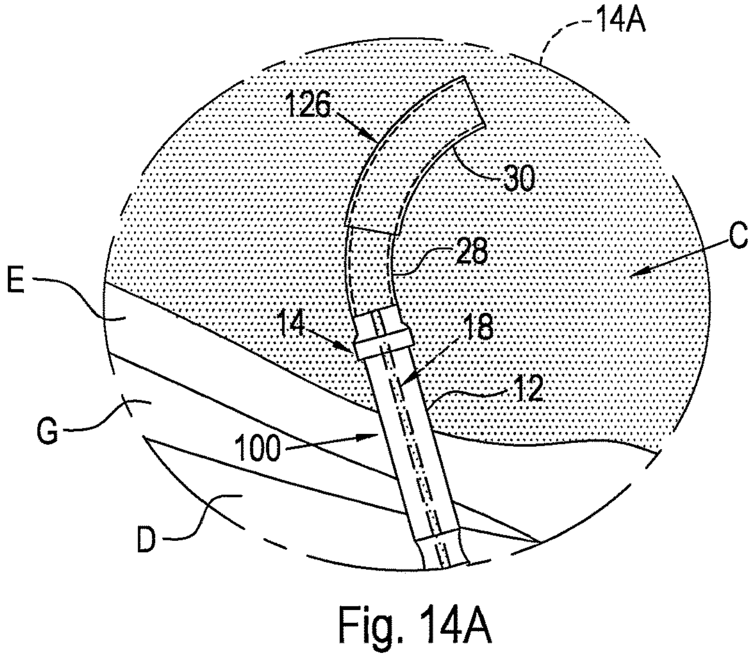
Figure 15:
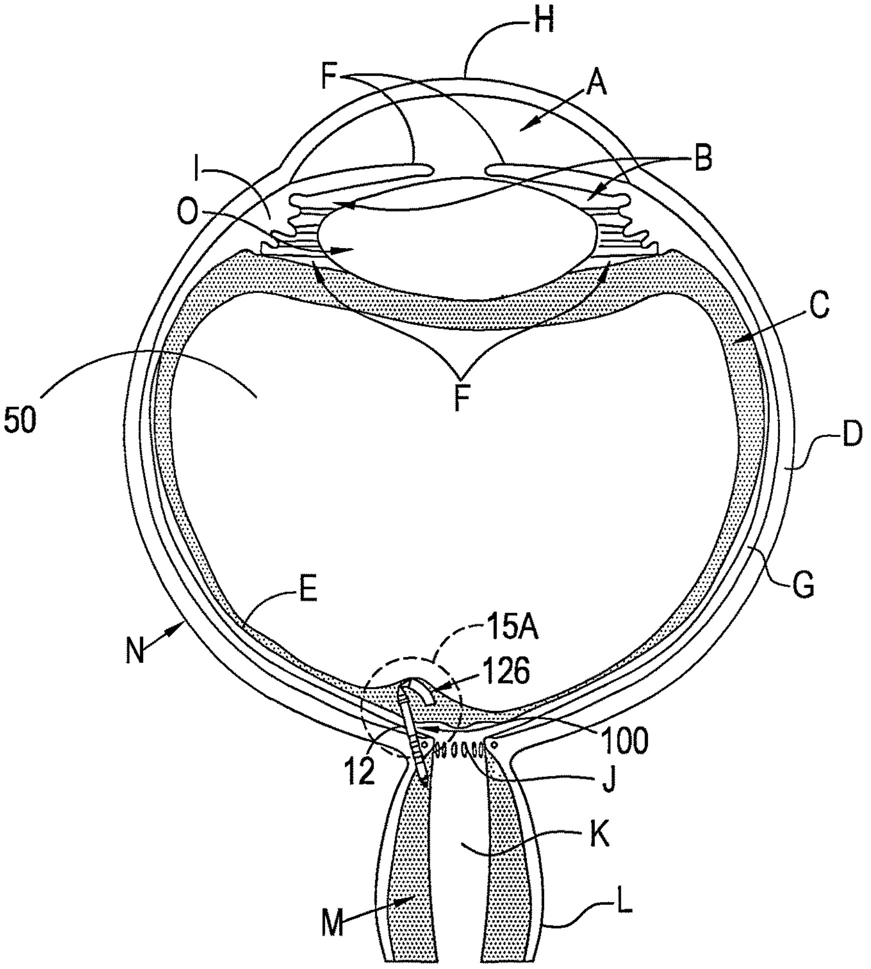
Figure 15A:
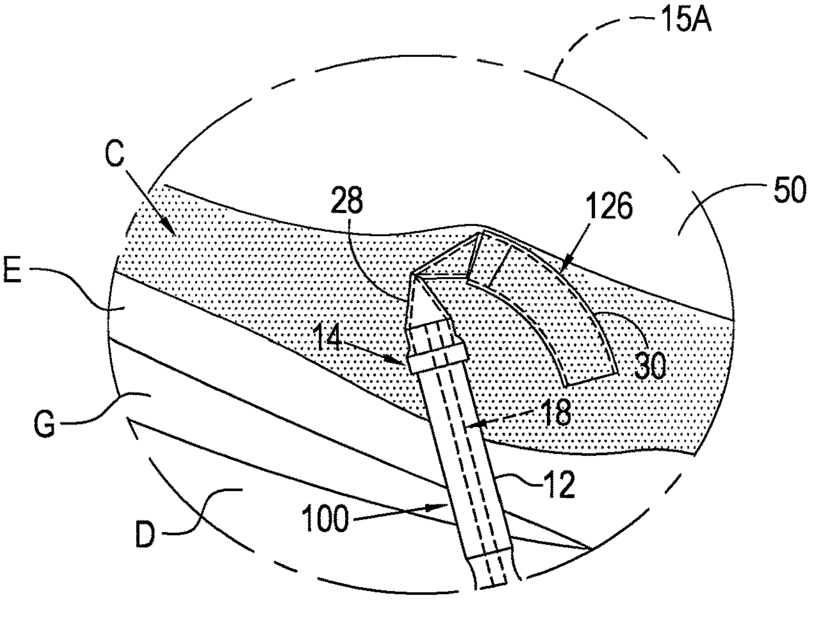
Figure 16:
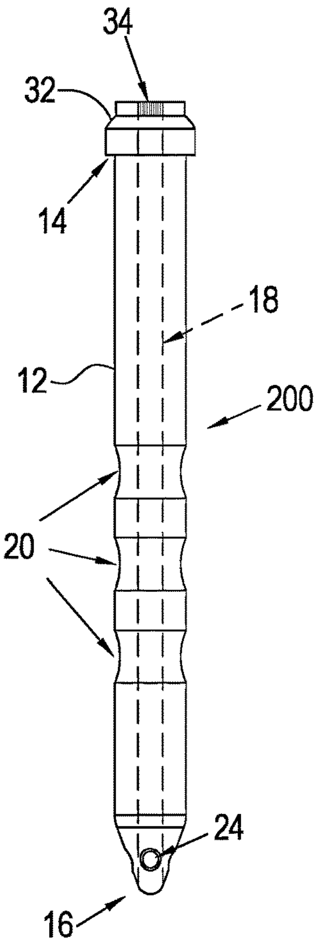
FIG. 16 shows a side view of a second embodiment of a shunt in accordance with the invention.
Figure 17:
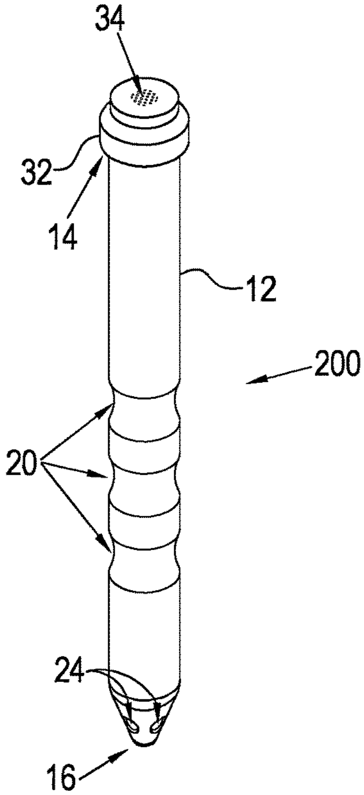
FIG. 17 shows a three-dimensional view of the shunt of FIG. 16.
Figure 18:
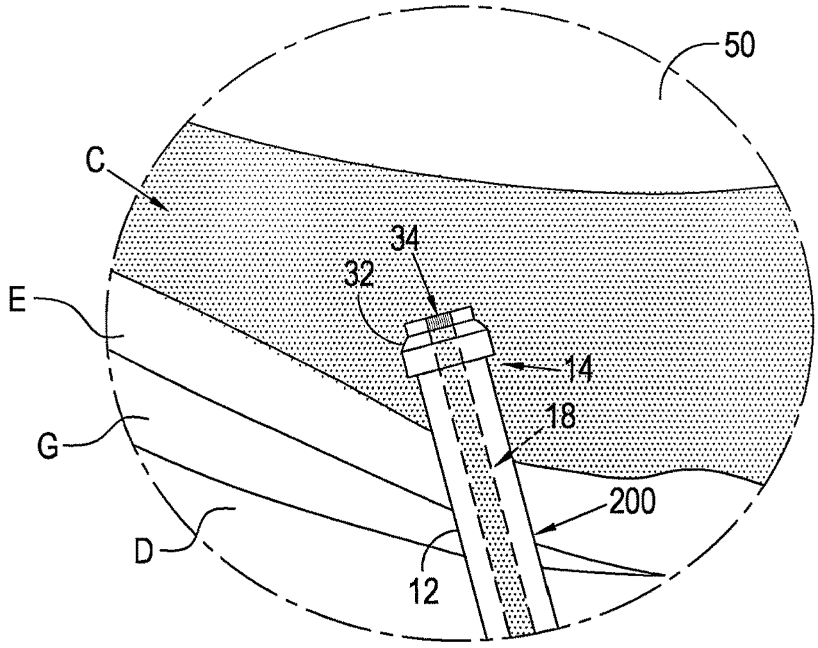
FIGS. 18 and 19 show enlarged fragmentary side views of the shunt of FIG. 16 implanted showing the lumen open and occluded by a gas bubble, respectively.
Figure 19:
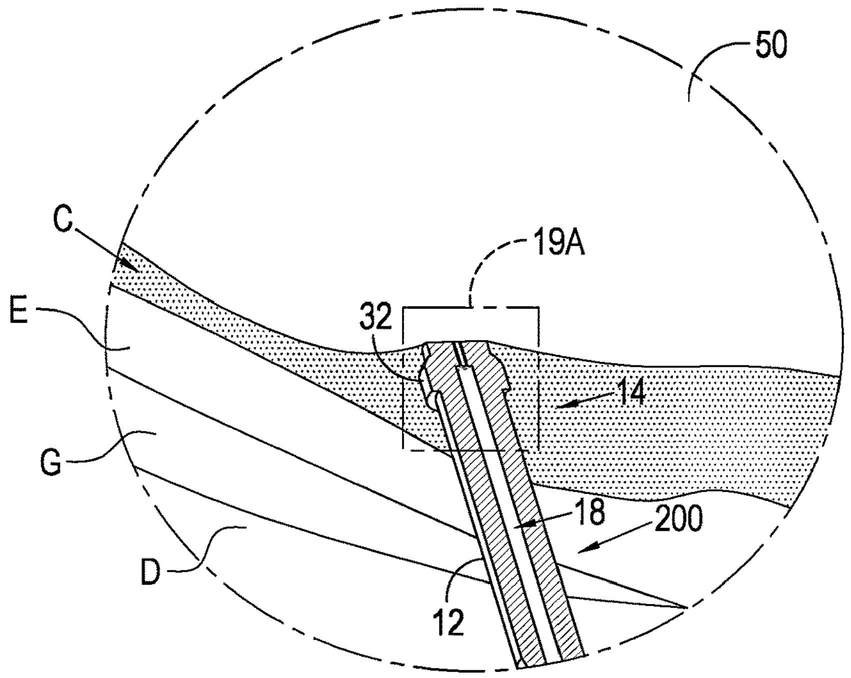
Figure 19A:
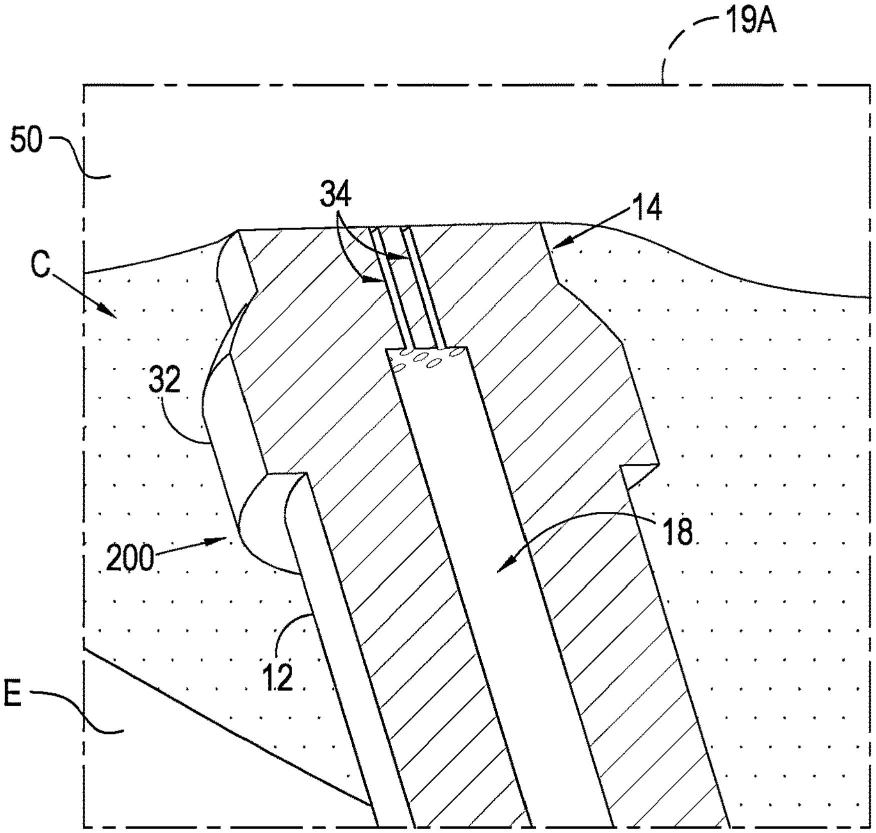
FIG. 19A shows enlarged fragmentary side view of detail 19A of FIG. 19.

The shunt 10 further includes occlusion means comprising a valve member in the form of a flap valve 26 which is hingedly connected to the tubular body at its proximal end. The flap valve 26 is hingedly displaceable between an open position (as shown in FIGS. 2 and 3) wherein the flap is spaced from the opening 22 at the proximal end of the tubular body and a closed position (as shown in FIGS. 4 and 5) wherein the opening 22 is closed, completely occluding the lumen 18. The flap valve 26 is connected to the tubular body in an arrangement wherein the flap valve is biased into the open position.

With reference to FIGS. 6-8A, the manner in which the shunt 10 is implanted and used is illustrated.

A method for treating glaucoma in a patient during and/or after vitreoretinal surgery, using the shunt 10, in accordance with the invention, includes:

making at least one incision in the pars plana region of the sclera;

removing the vitreous jelly from the vitreous cavity via the incision and replacing it with a saline solution;

advancing the distal end of the shunt through retinal nerve fibres and scleral tissue to enter the orbital subarachnoid space between the optic nerve and optic nerve sheath;

leaving the proximal end of the shunt within the vitreous cavity; and replacing an amount of saline solution in the vitreous cavity with a surgical tamponading agent in the form of a gas or oil.

The tamponading agent is in the form of a biocompatible gas or silicone oil bubble 50.

The shunt 10 is inserted inferiorly away from temporal paraoptic macular region, away from the PSPCA's and externally of the CZH blood vessel region. When inserting the shunt it is important to limit damage to important retinal nerve fibres as the shunt passes through retinal nerve fibres en route to the subarachnoid space. It is also important to prevent damage to the optic nerve head blood supply by avoiding damage to the PSPCA's and CZH en route to the subarachnoid space. The non-cutting tip of the distal end of the shunt and point of insertion plays an important role in this regard.

There is a tendency for surgical tamponades in the vitreous cavity to flow down the pressure gradient into the subarachnoid space. Here, they may cause injury to the optic nerve due to sudden increases in pressure from gaseous passage or inflammatory responses from silicone oil. The premature loss of tamponade from the vitreous cavity may also result in recurrence of retinal detachment.

The flap valve 26 is hingedly displaceable between a closed position wherein the flap completely occludes the lumen 18 when acted upon by the gas or oil bubble 50, preventing the gas or oil bubble from passing into the lumen and an open position wherein the lumen is not occluded, allowing aqueous fluid to flow along the lumen in order to adequately regulate intraocular pressure.

With reference to FIGS. 9-15A, a second example of the first embodiment of a shunt in accordance with the invention, is designated by the reference numeral 100. The shunt 100 is similar to the shunt 10 with a difference being that the shunt 100 has a differently configured valve member. Features of the shunt 100 which are the same as and/or similar to those of the shunt 10 are designated by the same and/or similar reference numerals in FIGS. 9-15A. The shunt 100 is implantable in the same manner as the shunt 10 and includes a tubular body 12 having a proximal end 14 which is implantable in the vitreous cavity C of a patient and a distal end 16 which is implantable in the subarachnoid space M of the patient. The tubular body defines a lumen 18 extending between the distal and proximal ends.

The shunt defines three stop formations in the form of longitudinally-spaced circumferential grooves 20 for resisting migration of the tubular body following insertion of the tubular body into the subarachnoid space.

A distal end region of the tubular body is tapered towards the distal end 16 of the tubular body. The distal end of the tubular body has a pencil-point, non-cutting surface profile.

The tubular body defines a proximal opening at the proximal end 14, leading into the lumen. The tubular body defines four distal openings 24 in a side wall of the distal end region, leading into the lumen.

The tubular body is of a biocompatible material polymer and may incorporate an elutable therapeutic substance such as an antibiotic substance for preventing the spread of an infection between the ocular chamber and the subarachnoid space or an anticlotting agent for preventing blockage of adjacent blood vessels or the lumen of the tubular body by blood clots.

The shunt 100 further includes occlusion means comprising a valve member in the form of a flexible tube valve 126 which is sealingly connected to the tubular body at its proximal end 14. The tube valve 126 defines an internal passage 118 which is in flow communication with the lumen 18 of the tubular body 12. The tube valve is configured to bend and as such is resiliently deformable. More specifically, the tube valve comprises a resiliently deformable first tube valve element 28 which is sealingly connected to the tubular body 12 at its proximal end and a deformable second tube valve element 30 which is connected to an end of the first tube valve element. The internal passage 118 extends through the first and second tube valve elements and is in flow communication with the lumen 18 of the tubular body 12. The second tube valve element 30 is of a relatively stiffer construction than the construction of the first tube valve element 28, thereby providing the tube valve 126 with a structure having variable stiffness wherein a distal end region of the tube valve defined by the second tube valve element 30 is stiffer than a proximal end region of the tube valve defined by the first tube valve element 28. The purpose of the variable stiffness will be explained in further detail below.

More specifically, the second tube valve element is resiliently displaceable between a valve closing position wherein the second tube valve element is bent when acted upon by the gas or oil bubble 50, causing a bending force to be exerted on the first tube valve element resulting in kinking of the first tube valve element and causing the passage 118 defined by the first tube valve element to at least partially occlude, thereby preventing the gas or oil bubble from passing into the passage 18 and the lumen 18 of the tubular body 12; and a valve opening position wherein the second tube valve element is not acted upon by the gas or oil bubble, allowing the first tube valve element to return to a naturally open position wherein the passage 118 defined thereby is not occluded, allowing aqueous fluid to flow along the lumen 18 of the tubular body 12 in order to adequately regulate intraocular pressure.

With reference to FIGS. 16-19A, a second embodiment of a shunt in accordance with the invention, is designated by the reference numeral 200. The shunt 200 is similar to the shunts 10 and 100 with a difference being that the shunt 200 has differently configured occlusion means. Features of the shunt 200 which are the same as and/or similar to those of the shunt 10 are designated by the same and/or similar reference numerals in FIGS. 16-19. The shunt 200 is implantable in the same manner as the shunts 10 and 100 and includes a tubular body 12 having a proximal end 14 which is implantable in the vitreous cavity C of a patient and a distal end 16 which is implantable in the subarachnoid space M of the patient. The tubular body defines a lumen 18 extending between the distal and proximal ends.

The shunt 200 defines three stop formations in the form of longitudinally-spaced circumferential grooves 20 for resisting migration of the tubular body following insertion of the tubular body into the subarachnoid space.

A distal end region of the tubular body is tapered towards the distal end 16 of the tubular body. The distal end of the tubular body has a pencil-point, non-cutting surface profile.

The tubular body 12 defines a proximal opening at the proximal end 14, leading into the lumen. The tubular body defines four distal openings 24 in a side wall of the distal end region, leading into the lumen.

The tubular body is of a biocompatible material polymer and may incorporate an elutable therapeutic substance such as an antibiotic substance for preventing the spread of an infection between the ocular chamber and the subarachnoid space or an anticlotting agent for preventing blockage of adjacent blood vessels or the lumen of the tubular body by blood clots.

The shunt 200 further includes occlusion means comprising a foraminous occlusion body 32 which is fitted onto the proximal end of the tubular body 12. The occlusion body 32 defines a number of micro-passages 34 which are in flow communication with the lumen 18 of the tubular body.

The shunt 200 is adapted for use in vitreoretinal surgery involving the use of a tamponading agent comprising a gas or oil bubble 50. The micro-passages are configured in terms of their size and number to provide sufficient surface tension and viscosity resistance in order to prevent tamponading agents comprising gas bubbles or oil bubbles from passing through the micro-passages into the lumen, yet allow sufficient aqueous fluid from the vitreous cavity to travel along the micro-passages into the lumen 18 in order to regulate intraocular pressure. This configuration permits the micro-passages 34 to be used to regulate intraocular pressures in a range between 5 mmHg and 60 mmHg. The occlusion body may be of a hydrophilic material for use with an oil or gas bubble tamponading agent for promoting a flow of aqueous fluid into the lumen. For use with an oil bubble tamponading agent, the occlusion body may additionally or alternatively, be of an oleophobic material for resisting a flow of oil into the lumen.

Figure 20:
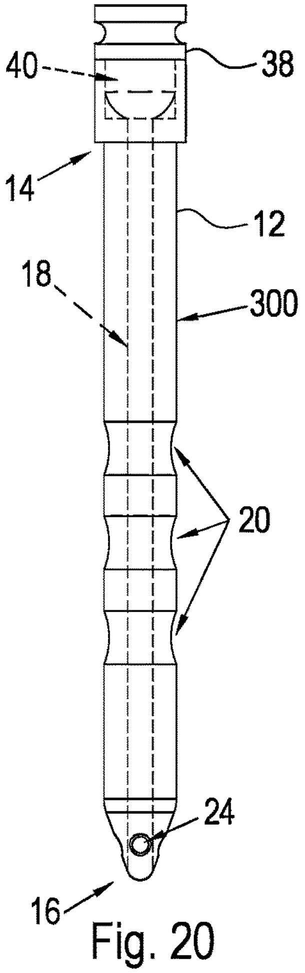
FIG. 20 shows a side view of a third embodiment of a shunt in accordance with the invention.
Figure 21:
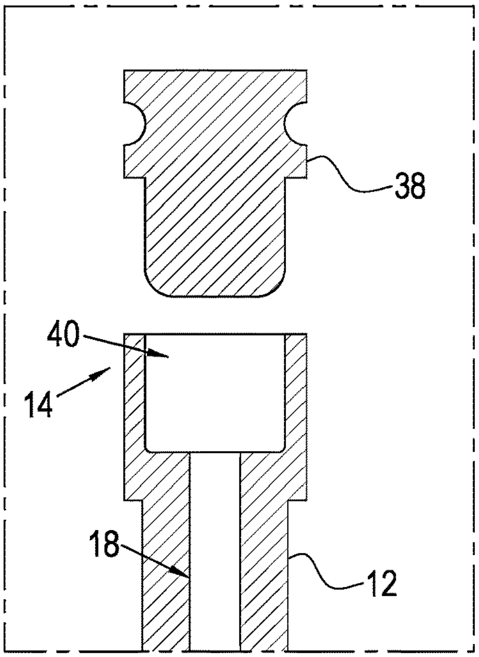
FIG. 21 shows an enlarged fragmentary exploded sectional side view of the shunt of FIG. 20.
Figure 22:
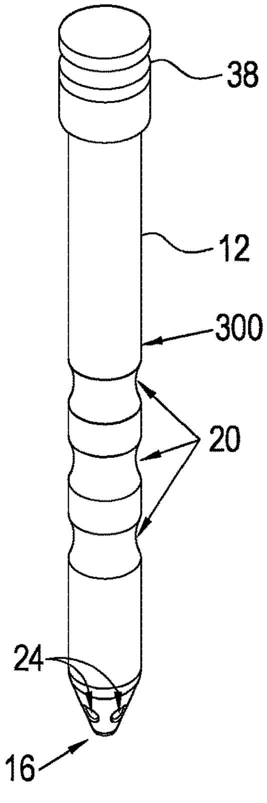
FIG. 22 shows a three-dimensional view of the shunt of FIG. 20.

With reference to FIGS. 20 to 22, a third embodiment of a shunt in accordance with the invention, is designated by the reference numeral 300. The shunt 300 is similar to the shunts 10, 100 and 200 with a difference being that the shunt 300 has a differently configured occlusion means. Features of the shunt 300 which are the same as and/or similar to those of the shunt 10 are designated by the same and/or similar reference numerals in FIGS. 16-19. The shunt 300 is implantable in the same manner as the shunts 10, 100 and 200 and includes a tubular body 12 having a proximal end 14 which is implantable in the vitreous cavity C of a patient and a distal end 16 which is implantable in the subarachnoid space M of the patient. The tubular body defines a lumen 18 extending between the distal and proximal ends.

The shunt 300 defines three stop formations in the form of longitudinally-spaced circumferential grooves 20 for resisting migration of the tubular body following insertion of the tubular body into the subarachnoid space.

A distal end region of the tubular body 12 is tapered towards the distal end 16 of the tubular body. The distal end of the tubular body has a pencil-point, non-cutting surface profile.

The tubular body defines a proximal opening at the proximal end 14, leading into the lumen. The tubular body defines four distal openings 24 in a side wall of the distal end region, leading into the lumen.

The tubular body is of a biocompatible material polymer and may incorporate an elutable therapeutic substance such as an antibiotic substance for preventing the spread of an infection between the ocular chamber and the subarachnoid space or an anticlotting agent for preventing blockage of adjacent blood vessels or the lumen of the tubular body by blood clots.

The shunt 200 further includes occlusion means comprising a plug 38 which is removably attached to the proximal end of the tubular body in order to completely occlude the lumen, preventing the tamponading agent from passing into the lumen. More specifically, the tubular body defines a socket 40 at its proximal end, into which the plug 38 is sealingly fitted during a vitreoretinal surgical procedure by a surgeon and thereafter removed once the tamponading agent is no longer present in the vitreous cavity, allowing aqueous to drain into the subarachnoid space via the lumen 18.

The invention extends to a fourth embodiment of a shunt in accordance with the invention, wherein the shunt is adapted for use in vitreoretinal surgery involving the use of a tamponading agent, and wherein the occlusion means comprises a dissolvable membrane which is attached to the tubular body 12 at its proximal end 14 so as to cover the proximal end, thereby occluding the lumen and preventing the tamponading agent from passing into the lumen. More specifically, the membrane is of a material which dissolves over a period of time so as to no longer occlude the lumen of the tubular body, coinciding with the tamponading agent no longer being present.

The invention extends to a fifth embodiment of a shunt in accordance with the invention, wherein the shunt is adapted for use in vitreoretinal surgery involving the use of a tamponading agent, the occlusion means may comprise a laserable membrane which is attached to the proximal end 14 of the tubular body 12 in order to occlude the lumen, preventing the tamponading agent from passing into the lumen. More specifically, the membrane is punctured by a surgeon using a laser once the tamponading agent is no longer present in the vitreous cavity.

The shunts and the method described hereinabove are effective in treating glaucoma in a patient by allowing for drainage for excess aqueous fluid from the ocular chambers into the orbital subarachnoid space during and after vitreoretinal surgery involving the use of a gas or oil tamponading agent.

What is claimed is:

1. A method for treating glaucoma in a patient during and/or after vitreoretinal surgery, the method including:

providing a shunt for treating glaucoma in a patient during and/or after vitreoretinal surgery involving use of a tamponading agent, the shunt including a tubular body having a proximal end which is implantable in an ocular chamber of the patient and a distal end which is implantable in an extra-ocular space of the patient, the tubular body defining a lumen extending between the distal and proximal ends, the shunt including occlusion means for at least partially occluding the lumen so as to prevent the tamponading agent from entering the extra-ocular space;

making at least one incision in a pars plana region of a sclera of the patient;

removing vitreous jelly from a vitreous cavity via the incision and replacing the vitreous jelly with a saline solution;

advancing the distal end of the shunt through retinal nerve fibres and scleral tissue to enter an orbital subarachnoid space between an optic nerve and an optic nerve sheath;

leaving the proximal end of the shunt within the vitreous cavity; and replacing an amount of saline solution in the vitreous cavity with the surgical tamponading agent in the form of gas or oil.

2. The method as claimed in claim 1, wherein the distal end of the shunt is implantable in the subarachnoid space of the patient, the distal end of the shunt being advanced through the scleral tissue in the inferior or superior quadrants approximately 0.5-1.5 mm from an optic nerve head in order to avoid important blood vessels.

3. The method as claimed in claim 1, wherein the distal end of the shunt is implantable in the subarachnoid space of the patient, the distal end of the shunt being advanced through the retinal nerve fibres in inferior, medial or superior quadrants to limit damage to important macular retinal nerve fibres.

* * * * *